United States Patent [19]
Kasting et al.

[11] Patent Number: 5,434,144
[45] Date of Patent: Jul. 18, 1995

[54] METHODS OF USING CYCLIC POLYANIONIC POLYOL DERIVATIVES FOR REGULATING SKIN WRINKLES

[75] Inventors: Gerald B. Kasting, Wyoming; John M. Gardlik, Cincinnati, both of Ohio

[73] Assignee: The Procter & Gamble Company, Cincinnati, Ohio

[21] Appl. No.: 206,472

[22] Filed: Mar. 4, 1994

[51] Int. Cl.$^6$ .............................................. A01N 57/26
[52] U.S. Cl. ...................................... 514/76; 514/120; 514/143; 514/557; 514/690; 514/709; 514/738
[58] Field of Search .................. 514/76, 120, 143, 557, 514/690, 709, 738

[56] References Cited

U.S. PATENT DOCUMENTS

| | | | |
|---|---|---|---|
| 3,523,998 | 8/1970 | Wolffe et al. | 424/78 |
| 4,207,339 | 6/1980 | Henmi et al. | 424/315 |
| 4,215,143 | 7/1980 | Henmi et al. | 424/315 |
| 5,268,176 | 12/1993 | Znaiden et al. | 424/401 |

FOREIGN PATENT DOCUMENTS

| | | | |
|---|---|---|---|
| 1066181A | 11/1992 | China | A61K 7/48 |
| 217413 | 10/1986 | European Pat. Off. | A61K 7/48 |
| 49-43949 | 9/1972 | Japan | 16/87 C |
| 49-9742 | 3/1974 | Japan | A61K 7/00 |
| 53-113030 | 10/1978 | Japan | A61K 31/095 |
| 54-19942 | 2/1979 | Japan | A61K 31/255 |
| 54-61153 | 5/1979 | Japan | A61K 31/255 |
| 4-290808 | 10/1992 | Japan | A61K 7/00 |
| WO89/05645 | 6/1989 | WIPO | A61K 31/715 |

OTHER PUBLICATIONS

Morel, N. et al., J. Cell. Physiol. (1989) 141 (3) 653–9.
Rosenbach, T. et al., Arch. Dermatol. Res. (1993) 285 (7) 393–6.
Tang, W. et al., J Invest Dermatol (1989) 92(1), 72–7.
Lei, Xuejun, "Extraction of Phytic Acid and its Application in Ordinary Chemical Engineering", *Riyong Huaxue Gongye,* vol. 5, pp. 223–224, 1989.

*Primary Examiner*—Paul J. Killos
*Attorney, Agent, or Firm*—John M. Howell; Milton B. Graff, IV; David L. Suter

[57] ABSTRACT

The subject invention relates to methods of regulating skin wrinkles and/or atrophy in mammalian skin comprising topically applying to the skin of a mammal in need of treatment a composition comprising a safe and effective amount of a cyclic polyanionic polyol derivative having the structure:

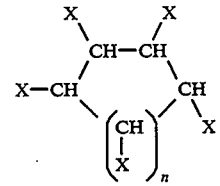

wherein n is an integer from 1 to 3; and each X is, independently, selected from the group consisting of $OSO_3^-$, $OPO_3^=$, $SO_3^-$, $PO_3^=$, $CO_2^-$, and OH; with at least 3 X's being other than OH.

21 Claims, No Drawings

METHODS OF USING CYCLIC POLYANIONIC POLYOL DERIVATIVES FOR REGULATING SKIN WRINKLES

TECHNICAL FIELD

The present invention relates to the field of treating aged skin. Specifically, the invention relates to novel methods of using certain compounds for effacing, reducing and/or preventing wrinkles in mammalian skin.

BACKGROUND OF THE INVENTION

Skin is subject to abuse by many extrinsic (environmental) factors as well as intrinsic (aging) factors. A common extrinsic factor is exposure to ultraviolet radiation. Whether extrinsic or intrinsic, the abuse results in wrinkling of the skin. To many people, skin wrinkles are a reminder of the disappearance of youth. As a result, the reduction of wrinkles has become a booming business in youth-conscious societies. Treatments range from cosmetic creams and moisturizers to various forms of cosmetic surgery.

Chronological aging results in the thinning and general degradation of skin. As the skin naturally ages, there is a reduction in the cells and blood vessels that supply the skin. There is also a flattening of the dermal-epidermal junction which results in weaker mechanical strength of this junction. As a consequence, older persons are more susceptive to blister formation in cases or mechanical trauma or disease processes. (See Oikarinen, "The Aging of Skin: Chronoaging Versus Photoaging", *Photodermatol. Photoimmunol. Photomed.*, Vol. 7, pp 3–4 (1990).

It is an object of the subject invention to provide methods for regulating skin wrinkles and/or atrophy in mammalian skin. It is a further object of the subject invention to provide topical compositions for regulating skin wrinkles in mammalian skin.

SUMMARY OF THE INVENTION

The subject invention involves methods of regulating skin wrinkles and/or atrophy in mammalian skin comprising topically applying to the skin of a mammal in need of treatment a composition comprising a safe and effective amount of a cyclic polyanionic polyol derivative having the structure:

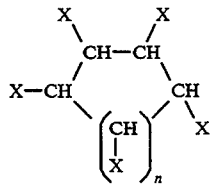

wherein n is an integer from 1 to 3 and each X is, independently, selected from the group consisting of $OSO_3^-$, $OPO_3^=$, $SO_3^-$, $PO_3^=$, $CO_2^-$, and $OH$. At least three are other than $OH$. The compositions also contain an appropriate amount pharmaceutically-acceptable cations so as to balance the charge on the polyol derivatives. Examples of such cations include (but are not limited to) $H^+$, $Na^+$, $K^+$, $Ca^{++}$, $Mg^{++}$, $Al_2(OH)_5^+$, $NH_4^+$, $(HOCH_2CH_2)_3NH^+$, $(CH_3CH_2)_3NH^+$, $HOCH_2(CH_3)_2CNH_3^+$, $(HOCH_2)_3CNH_3^+$, $CH_3(HOCH_2)_2CNH_3^+$, $CH_3CH_2(HOCH_2)_2CNH_3^+$, $(CH_3CH_2)_4N^+$, $C_{16}H_{33}(CH_3)_3N^+$ and $(N-C_{16}H_{33})C_5H_4N^+$, and mixtures thereof.

DETAILED DESCRIPTION OF THE INVENTION

As used herein, "topical application" means directly laying on or spreading on outer skin.

As used herein, "pharmaceutically-acceptable" means that salts, drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

As used herein, "safe and effective amount" means an amount of compound or composition sufficient to significantly induce a positive modification in the condition to be treated, but low enough to avoid serious side effects (at a reasonable ratio), within the scope of sound medical judgment. The safe and effective amount of the compound or composition will vary with the particular condition being treated, the age and physical condition of the patient being treated, the severity, of the condition, the duration of the treatment, the nature of concurrent therapy, the specific compound or composition employed, the particular pharmaceutically-acceptable carrier utilized, and like factors within the knowledge and expertise of the attending physician.

As used herein, "anti-wrinkle agent" means a cyclic polyanionic polyol derivative, or a pharmaceutically-acceptable salt thereof, as defined hereinbelow.

As used herein, "regulating wrinkles" means preventing, retarding, arresting, or reversing the process of wrinkle formation or diminishing the appearance and/or size wrinkles in mammalian skin. Other manifestations often associated with wrinkles are a smoother feel and/or improved texture to the skin.

As used herein "regulating atrophy" means preventing, retarding arresting or reversing the process of atrophy in mammalian skin.

As used herein, all percentages are by weight unless otherwise specified.

Active Agent

The subject invention involves a method for regulating wrinkles and/or atrophy in mammalian skin by topically applying to the skin a safe and effective amount of a cyclic polyanionic polyol or derivative having the structure:

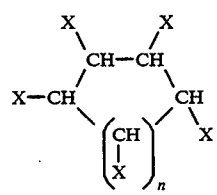

wherein n is 1, 2 or 3 and each X is, independently, selected from the group consisting of $OSO_3^-$, $OPO_3^{2-}$, $SO_3^-$, $PO_3^{2-}$, $CO_2^-$, and $OH$. At least three X are other than $OH$, more preferably at least four X, more preferably still at least five X, most preferably six X. When n is 1 or 2, all X are, preferably other than $OH$. All X which are other than $OH$ are preferably the same.

The active agent is neutralized by an appropriate amount of a pharmaceutically-acceptable cation so as to balance the charge. The cation is selected from a group including (but are not limited to) H+, Na+, K+, Ca++, Mg++, Al$_2$(OH)$_5$+, NH$_4$+, (HOCH$_2$CH$_2$)$_3$NH+, (CH$_3$CH$_2$)$_3$NH+, HOCH$_2$(CH$_3$)$_2$CNH$_3$+, (HOCH$_2$)$_3$CNH$_3$+, CH$_3$(HOCH$_2$)$_2$CNH$_3$+, CH$_3$CH$_2$(HOCH$_2$)$_2$CNH$_3$+, (CH$_3$CH$_2$)$_4$N+, C$_{16}$H$_{33}$(CH$_3$)$_3$N+ and (N—C$_{16}$H$_{33}$)C$_5$H$_4$N+, and mixtures thereof.

Preferred n is 1 or 2; more preferred n is 2.

Preferred X is OSO$_3$— or OPO$_3$$^{2-}$; more preferred X is OPO$_3$$^{2-}$. All non-OH X's are preferably the same.

Preferred cations are H+, Na+, K+, NH$_4$+, (HOCH$_2$CH$_2$)$_3$NH+, HOCH$_2$(CH$_3$)$_2$CNH$_3$+, (HOCH$_2$)$_3$CNH$_3$+, CH$_3$(HOCH$_2$)$_2$CNH$_3$+, or mixtures thereof; more preferred are H+, Na+, NH$_4$+, HOCH$_2$(CH$_3$)$_2$CNH$_3$+, (HOCH$_2$)$_3$CNH$_3$+, CH$_3$(HOCH$_2$)$_2$CNH$_3$+, or mixtures thereof.

Preferred active agents of the subject invention include:

1,2,3,4,5,6-cyclohexanehexalphosphoric acid (scyllo, myo or other inositol hexakis phosphoric acid derivatives), having the structure:

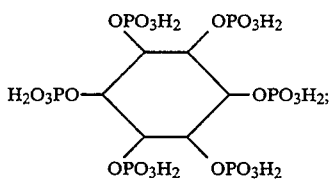

myo-inositol hexakisphosphate, calcium salt
myo-inositol hexakisphosphate, dimagnesium tetrapotassium salt
myo-inositol hexakisphosphate, magnesium potassium salt
myo-inositol hexakisphosphate, dipotassium salt
myo-inositol hexakisphosphate, monopotassium salt
myo-inositol hexakisphosphate, dodecasodium salt
myo-inositol hexakisphosphate, triethanolamine salt
myo-inositol hexakisphosphate, ammonium salt
myo-inositol hexakisphosphate, cetylpyridinium salt
myo-inositol hexakisphosphate, cetyltrimethylammonium salt
myo-inositol-1,3,4,5,6-pentakisphosphate, ammonium salt
myo-inositol-1,2,5,6-tetrakisphosphate, ammonium salt
myo-inositol-1,3,4,5-tetrakisphosphate, ammonium salt
myo-inositol-1,3,4,6-tetrakisphosphate, ammonium salt
myo-inositol-3,4,5,6-tetrakisphosphate, ammonium salt
myo-inositol-1,4,5,-trisphosphate, potassium salt
myo-inositol-1,3,4-trisphosphate, ammonium salt
myo-inositol-1,5,6-trisphosphate, ammonium salt
myo-inositol-2,4,5-trisphosphate, ammonium salt
1,2,3,4,5,6-cyclohexanehexolsulfuric acid (scyllo, myo or other inositol hexakis sulfuric acid derivatives), having the structure:

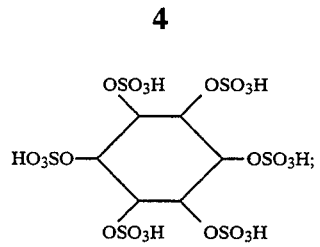

myo-inositol hexakissulfate, sodium salt
myo-inositol hexakissulfate, hexasodium salt
myo-inositol hexakissulfate, potassium salt
myo-inositol hexakissulfate, hexapotassium salt
myo-inositol hexakissulfate, ammonium salt
myo-inositol hexakissulfate, triethanolamine salt
myo-inositol hexakissulfate, cetylpyridinum salt
myo-inositol hexakissulfate, cetyltrimethylammonium salt
myo-inositol pentakissulfate
myo-inositol tetrakissulfate
myo-inositol trissulfate
myo-inositol-1,2,3-trissulfate-4,5,6-trisphosphate
1,2,3,4,5,6-cyclohexanehexaphosphonic acid, having the structure:

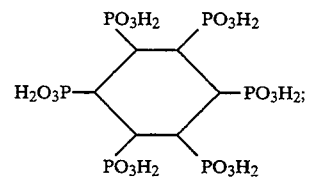

1,2,3,4,5,6-cyclohexanehexasulfonic acid, having the structure:

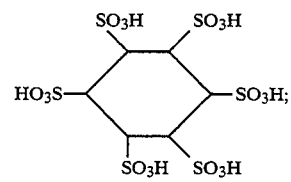

1,2,3,4,5,6-cyclohexanehexacarboxylic acid, having the structure:

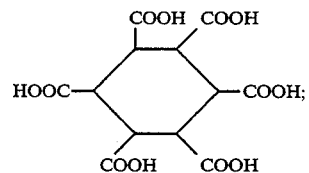

1,2,3,4,5-cyclopentanepentalsulfuric acid, having the structure:

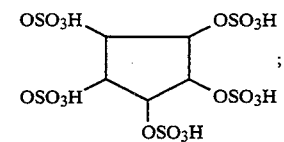

1,2,3,4,5-cyclopentanepentalphosphoric acid, having the structure:

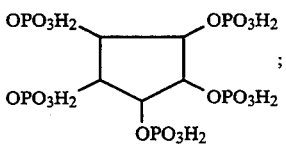

1,2,3,4,5,6,7-cycloheptaneheptalsulfuric acid, having the structure:

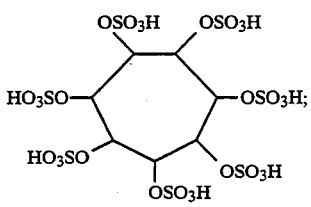

1,2,3,4,5,6,7-cycloheptaneheptalphosphoric acid, having the structure:

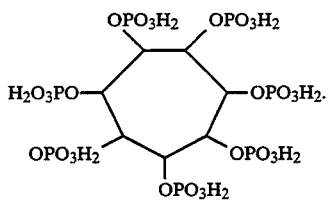

More preferred active agents include myo-inositol hexakis phosphoric acid, myo-inositol hexakis sulfuric acid and myo-inositol 1,2,3 trissulfate-4,5,6-trisphosphate. Even more preferred active agents included myo-inositol hexakis phosphoric acid and myo-inositol hexakis sulfuric acid. The most preferred active is myo-inositol hexakis phosphoric acid.

Preferred delivery modes of the subject compounds into the skin are passive diffusion and cathodal iontophoresis (application of an electric field, either pulsed or continuous, having a polarity such as to drive anions into the skin); more preferred is passive diffusion.

Pharmaceutical Compositions

The methods of the subject invention preferably involve topical application of a composition to mammalian skin, the composition comprising an active anti-wrinkle agent or mixture of active anti-wrinkle agents as described hereinabove and a pharmaceutically-acceptable topical carrier.

The term "pharmaceutically-acceptable topical carrier", as used herein, means one or more compatible solid or liquid filler diluents which are suitable for topical administration to a human or lower animal. Pharmaceutically-acceptable topical carriers must be of sufficiently high purity and sufficiently low toxicity to render them suitable for topical administration to the human or lower animal being treated. A safe and effective amount of carrier is preferably from about 50% to about 99.99%, more preferably from about 90% to about 99% of the composition.

Variations in formulation of these carriers will result in a wide variety of products which fall within the scope of the subject invention.

Topical Compositions

The topical compositions useful in the subject invention may be made into a wide variety of product types. These include, but are not limited to lotions, creams, beach oils, gels, sticks, sprays, ointments, pastes, mousses and cosmetics. These product types may comprise several types of carrier systems including, but not limited to solutions, emulsions, gels and solids.

The topical compositions useful in the subject invention formulated as solutions typically include a pharmaceutically-acceptable aqueous or organic solvent. The terms "pharmaceutically-acceptable aqueous solvent" and "pharmaceutically-acceptable organic solvent" refer to a solvent which is capable of having dispersed or dissolved therein the anti-wrinkle agent, and possesses acceptable safety properties (e.g., irritation and sensitization characteristics). Water is a preferred solvent. Examples of suitable organic solvents include: propylene glycol, polyethylene glycol (200–600), polypropylene glycol (425–2025), glycerol, 1,2,4-butanetriol, dimethyl isosorbide, sorbitol esters, 1,2,6-hexanetriol, ethanol, isopropanol, butanediol, dimethyl isosorbide, butylene glycol monoethyl ether, and mixtures thereof. These solutions useful in the subject invention preferably contain from about 0.001% to about 20%, more preferably from about 0.1% to about 10%, more preferably still from about 0.5% to about 5%, also preferably from about 1% to about 4% of the anti-wrinkle agent, and preferably from about 80% to about 99.99%, more preferably from about 90% to about 99.9% of an acceptable aqueous or organic solvent.

Topical compositions of the subject invention preferably comprise less than 1% by weight of chloride ions, more preferably less than 0.5%, also preferably less than 0.1%. The subject compositions are, preferably, substantially free of carbonate ions. The subject compositions preferably comprise 0.1% or more of sulfate ions, more preferably 0.3% or more, also preferably 0.5% or more. The subject compositions preferably comprise 0.1% or more of inorganic phosphate, more preferably 0.3% or more, also preferably 0.5% or more. The subject compositions preferably comprise 0.1% or more of a combination of sulfate ions and inorganic phosphate, more preferably 0.3% or more, also preferably 0.5% or more.

If the topical compositions useful in the subject invention are formulated as an aerosol and applied to the skin as a spray-on, a propellant is added to a solution composition. Examples of propellants useful herein include, but are not limited to, the chlorinated, fluorinated and chloro-fluorinated lower molecular weight hydrocarbons. A more complete disclosure of propellants useful herein can be found in Sagarin, *Cosmetics Science and Technology*, 2nd Edition, Vol. 2, pp. 443–465 (1972).

Topical compositions useful in the subject invention may be formulated as a solution comprising an emollient. An example of a composition formulated in this way would be a beach oil product. Such compositions preferably contain from about 2% to about 50% of a topical pharmaceutically-acceptable emollient.

As used herein, "emollients" refer to materials used for the prevention or relief of dryness, as well as for the protection of the skin. A wide variety of suitable emollients are known and may be used herein. Sagarin, *Cosmetics, Science and Technology*, 2nd Edition, Vol. 1, pp. 32–43 (1972), incorporated herein by reference, contains numerous examples of suitable materials.

A lotion can be made from a solution carrier system. Lotions typically comprise from about 1% to about 20%, preferably from about 5% to about 10%, of an emollient; and from about 50% to about 90%, preferably from about 60% to about 80%, water.

Another type of product that may be formulated from a solution carrier system is a cream. A cream typically comprises from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may also comprise from about 2% to about 10% of an emollient plus from about 0.1% to about 2% of a thickening agent. A more complete disclosure of thickening agents useful herein can be found in Sagarin, *Cosmetics, Science and Technology*, 2nd Edition, Vol. 1, pp. 72-73 (1972).

If the carrier is formulated as an emulsion, preferably from about 1% to about 10%, more preferably from about 2% to about 5%, of the carrier system comprises an emulsifier. Emulsifiers may be nonionic, artionic or cationic. Suitable emulsifiers are disclosed in, for example, U.S. Pat. No. 3,755,560, issued Aug. 28, 1973, Dickert et al, U.S. Pat. No. 4,421,769, issued Dec. 20, 1983, Dixon et al.; and McCutcheon's *Detergents and Emulsifiers*, North American Edition, pages 317-324 (1986); the disclosures of which are incorporated herein by reference. Preferred emulsifiers are anionic or nonionic, although the other types may also be used.

Lotions and creams can be formulated as emulsions as well as solutions. Typically such lotions comprise from about 1% to about 20%, preferably from about 5% to about 10%, of an emollient; from about 25% to about 75%, preferably from about 45% to about 95%, water; and from about 0.1% to about 10%, preferably from about 0.5% to about 5%, of an emulsifier. Such creams would typically comprise from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type, as disclosed in U.S. Pat. No. 4,254,105, Fakuda et al., issued Mar. 3, 1981, incorporated herein by reference, are also useful in the subject invention. In general, such single or multiphase emulsions contain water, emollients and emulsifiers as essential ingredients. Triple emulsion carrier systems comprising an oil-in-water-in-silicone fluid emulsion composition as disclosed in U.S. Pat. No. 4,960,764, Figueroa, issued Oct. 2, 1990, are also useful in the subject invention.

Another emulsion carrier system useful in the topical compositions is a microemulsion carrier system. Such a system comprises from about 9% to about 15% squalane; from about 25% to about 40% silicone oil; from about 8% to about 20% of a fatty alcohol; from about 15% to about 30% of polyoxyethylene sorbitan monofatty acid (commercially available under the trade name Tweens) or other nonionics; and from about 7% to about 20% water.

Liposomal formulations are also useful compositions of the subject invention. Such compositions can be prepared by first combining an anti-wrinkle agent in water and then combining this solution with a phospholipid or phospholipid/lipid mixture such as dipalmitoylphosphatidyl choline and cholesterol according to the method described in Mezei & Gulasekharam, "Liposomes—A Selective Drug Delivery System for the Topical Route of Administration: Gel Dosage Form", *Journal of Pharmaceutics and Pharmacology*, Vol. 34 (1982), pp. 473-474, incorporated herein by reference, or a modification thereof. Nonionic surfactants or epidermal lipiris of suitable composition for forming liposomes may be substituted for the phospholipid. The liposome preparation is then incorporated into one of the above topical carrier systems (for example, a gel or an oil-in-water emulsion) in order to produce the liposomal formulation. Other compositions and pharmaceutical uses of topically applied liposomes are described in Mezei, M., "Liposomes as a Skin Drug Delivery System", *Topics in Pharmaceutical Sciences* (D. D. Breimer and P. Speiser, eds.), Elsevier Science Publishers B. V., New York, N.Y., 1985, pp. 345-358, incorporated herein by reference. The reverse-phase evaporation method as described in Szoka and Papahadjopoulos, "Procedure for Preparation of Liposomes with Large Internal Aqueous Space and High Capture by Reverse-Phase Evaporation", *Proceeding of the National Academy of Sciences*, Vol. 75, pp. 4194-4198 (1978), and also in DuPlessis, Egbaria, and Weiner, "Influence of Formulation Factors on the Deposition of Liposomal Components into the Different Strata of the Skin", *Journal of the Society of Cosmetic Chemists*, Vol. 43, pp. 93-100 (1992) may also be employed to make a particularly useful liposomal dispersion of the anti-wrinkle agent, and are incorporated herein by reference.

If the topical compositions useful in the subject invention are formulated as a gel or a cosmetic stick, such compositions can be formulated by the addition of a suitable amount of a thickening agent, as disclosed supra, to a cream or lotion formulation.

Topical compositions useful in the subject invention may also be formulated as makeup products, such as foundations. Foundations are solution or lotion-based with appropriate amounts of thickeners, pigments and fragrance.

The topical compositions useful in the subject invention may contain, in addition to the aforementioned components, a wide variety of additional oil-soluble materials and/or water-soluble materials conventionally used in topical compositions, at their art-established levels.

Various water-soluble materials may also be present in the compositions useful in the subject invention. These include humectants, proteins and polypeptides, preservatives and an alkaline agent. In addition, the topical compositions useful herein can contain conventional cosmetic adjuvants, such as dyes, opacifiers (e.g., titanium dioxide), pigments and perfumes.

The topical compositions useful in the subject invention may also include a safe and effective amount of a penetration enhancing agent. A preferred amount of penetration enhancing agent is from about 1% to about 5% of the composition. Examples of useful penetration enhancers, among others, are disclosed in U.S. Pat. Nos. 4,537,776, Cooper, issued Aug. 27, 1985; 4,552,872, Cooper et al., issued Nov. 12, 1985; 4,557,934, Cooper, issued Dec. 10, 1985; 4,130,667, Smith, issued Dec. 19, 1978; 3,989,816, Rhaadhyaksha, issued Nov. 2, 1976; 4,017,641, DiGiulio, issued Apr. 12, 1977; and 4,954,487, Cooper, Loomans & Wickett, issued Sep. 4, 1990. Additional penetration enhancers useful in the subject invention are disclosed in Cooper, E. R., "Effect of Decylmethylsulfoxide on Skin Penetration", *Solution Behavior of Surfactants*, Vol. 2 (Mittal and Fendler, eds.), Plenum Publishing Corp., 1982, pp. 1505–1516; Mahjour, M., B. Mauser, Z. Rashidbaigi & M. B. Fawzi, "Effect of Egg Yolk Lecithins and Commercial Soybean Lecithins on In Vitro Skin Permeation of Drugs", *Journal of Controlled Release*, Vol. 14 (1990), pp. 243–252; Wong, O., J. Huntington, R. Konishi, J. H. Rytting & T. Higuchi, "Unsaturated Cyclic Ureas as New Nontoxic Biodegradable Transdermal Penetration Enhancers I: Synthesis", *Journal of Pharmaceutical Sciences*, Vol. 77, No. 11 (November 1988), pp. 967–971; Williams, A. C. & B. W. Barry, "Terpenes and the Lipid-Protein-Partitioning Theory of Skin Penetration Enhancement", *Pharmaceutical Research*, Vol. 8, No. 1 (1991), pp. 17–24; and Wong, O., J. Huntington, T. Nishihata & J. H. Rytting, "New Alkyl N,N-Dialkyl-Substituted Amino Acetates as Transdermal Penetration Enhancers", *Pharmaceutical Research*, Vol. 6, No. 4 (1989), pp. 286–295. The above references are incorporated herein by reference.

Other conventional skin care product additives may also be included in the compositions useful in the subject invention. For example, collagen, hyaluronic acid, elastin, hydrolysates, primrose oil, jojoba oil, epidermal growth factor, soybean saponins, mucopolysaccharides, and mixtures thereof may be used.

Various vitamins may also be included in the compositions useful in the subject invention. For example, Vitamin A, and derivatives thereof, Vitamin $B_2$, biotin, pantothenic acid, Vitamin D, Vitamin E, and mixtures thereof may be used.

Cleaning Compositions

Skin cleaning compositions useful in the subject invention comprise, in addition to the anti-wrinkle agent, a cosmetically-acceptable surfactant. The term "cosmetically-acceptable surfactant" refers to a surfactant which is not only an effective skin cleanser, but also can be used without undue toxicity, irritation, allergic response, and the like. Furthermore, the surfactant must be capable of being commingled with the anti-wrinkle agent in a manner such that there is no interaction which would substantially reduce the efficacy of the composition for effacing or preventing skin wrinkles.

The skin cleaning compositions useful in the subject invention preferably contain from about 1% to about 90%, more preferably from about 5% to about 10%, of a cosmetically-acceptable surfactant. The physical form of the skin cleansing compositions is not critical. The compositions can be, for example, formulated as toilet bars, liquids, pastes, or mousses. Toilet bars are most preferred since this is the form of cleansing agent most commonly used to wash the skin.

The surfactant component of the compositions useful in the subject invention are selected from anionic, nonionic, zwitterionic, amphoteric and ampholytic surfactants, as well as mixtures of these surfactants. Such surfactants are well-known to those skilled in the detergency art.

The cleaning compositions useful in the subject invention can optionally contain, at their art-established levels, materials which are conventionally used in skin cleansing compositions.

Combination Actives

A. Sunscreens and Sunblocks

Regulation of skin wrinkling resulting from exposure to ultraviolet light can be achieved by using combinations of the anti-wrinkle agents together with sunscreens or sunblocks. Useful sunblocks include, for example, zinc oxide and titanium dioxide.

Photo damage by ultraviolet light is a predominant cause of skin wrinkling. Thus, for purposes of wrinkle prevention, the combination of an anti-wrinkle agent with a UVA and/or UVB sunscreen is desirable. The inclusion of sunscreens in compositions useful in the subject invention at low levels does not greatly reduce the tanning response of the user but enhances immediate protection against acute UV damage.

A wide variety of conventional sunscreening agents are suitable for use in combination with the anti-wrinkle agent. Sagarin, et at., at Chapter VIII, pages 189 et seq., of *Cosmetics Science and Technology*, disclose numerous suitable agents. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, octyl, and dipropyleneglycol esters); cinnamic acid derivatives (menthyl, octyl, 2-ethylhexyl, and benzyl esters, alphaphenyl cinnamonitrile; butyl cinnamoyl pyruvate); dihydroxycinnamic acid derivatives (umbelliferone, methylumbelliferone, methylaceto-umbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbitol) (6-propyl piperonyl) ether; hydroquinone; benzophenones (oxybenzene, sulfobenzone, dioxybenzone, benzoresorcinol, 2,2',4,4'-tetrahydroxybenzophenone, 2,2'-dihydroxy-4,4'-dimethoxybenzophenone, octabenzone; butylmethoxydibenzoylmethane; etocrylene; and 4-isopropyl-di-benzoylmethane.

Of these, 2-ethylhexyl-p-methoxycinnamate, 4,4'-t-butyl methoxydi-benzoylmethane, 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethylamino-benzoate, 2-phenylbenzimidazole-5-sulfonic acid, 2-(p-dimethylaminophenyl)-5-sulfonicbenzoxazoic acid and mixtures of these compounds, are preferred.

More preferred sunscreens useful in the compositions useful in the subject invention are 2-ethylhexyl-p-methoxycinnamate, butylmethoxydibenzoylmethane, 2-hydroxy-4-methoxybenzophenone, octyldimethyl-p-aminobenzoic acid and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl) methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

A safe and effective amount of sunscreen may be used in the anti-wrinkle agent compositions useful in the subject invention. The sunscreening agent must be compatible with the anti-wrinkle agent. The composition preferably comprises from about 1% to about 20%, more preferably from about 2% to about 10%, of a sun-screening agent. Exact amounts will vary depending upon the sunscreen chosen and the desired Sun Protection Factor (SPF).

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

B. Anti-Inflammatory Agents

In a preferred wrinkle regulating composition useful in the subject invention, an anti-inflammatory agent is included as an active along with the anti-wrinkle agent. The inclusion of an anti-inflammatory agent enhances the wrinkle regulating benefits of the compositions. The anti-inflammatory agent protects strongly in the UVA radiation range (though it also provides some UVB protection as well). The topical use of anti-inflammatory agents reduces photo-aging of the skin resulting from chronic exposure to UV radiation. (See U.S. Pat. No. 4,847,071, Bissett, Bush, and Chatterjee, issued Jul. 11, 1989, incorporated herein by reference; and U.S. Pat. No. 4,847,069, Bissett and Chatterjee, issued Jul. 11, 1989, incorporated herein by reference.)

A safe and effective amount of an anti-inflammatory agent may be added to the compositions useful in the subject invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc., of non-steroidal anti-inflammatory agents, reference may be had to standard texts, including *Anti-inflammatory and Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et al., Academic Press, New York (1974).

Specific non-steroidal anti-inflammatory agents useful in the composition invention include, but are not limited to:

1) the oxicams, such as piroxicam, isoxicam, tenoxicam, sudoxicam, and CP-14,304;

2) the salicylates, such as aspirin, disalcid, benorylate, trilisate, safapryn, solprin, diflunisal, and fendosal;

3) the acetic acid derivatives, such as diclofenac, fenclofenac, indomethacin, sulindac, tolmetin, isoxepac, furofenac, tiopinac, zidometacin, acematacin, fentiazac, zomepirac, clidanac, oxepinac, and felbinac;

4) the fenamates, such as mefenamic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic acids; and 6) the pyrazoles, such as phenylbutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Another class of anti-inflammatory agents which are useful in the compositions are the anti-inflammatory agents disclosed in U.S. Pat. No. 4,708,966, Loomans et al., issued Nov. 24, 1987. This patent discloses a class of nonsteroidal anti-inflammatory compounds which comprise specifically substituted phenyl compounds, especially substituted 2,6-di- tert-butyl phenol derivatives. For example, compounds selected from 4-(4'-pentyn-3'-one)-2,6-di+butylphenol; 4-(5'-hexynoyl)-2,6-di-t-butylphenol; 4-((S)-(−)-3'-methyl-5'-hexynoyl)-2,6-di-t-butylphenol; 4-((R)-(+)-3'-methyl-5'-hexynoyl)-2,6-di-t-butylphenol; and 4-(3',3'-dimethoxypropionyl)-2,6-di-t-butylphenol are useful in methods of the subject invention; 4-(5'-hexynoyl)-2,6-d-t-butylphenol is most preferred.

Yet another class of anti-inflammatory agents which are useful in the compositions are those disclosed in U.S. Pat. No. 4,912,248, Mueller, issued Mar. 27, 1990. This patent discloses compounds and diastereomeric mixtures of specific 2-naphthyl-containing ester compounds, especially naproxen ester and naproxol ester compounds, having two or more chiral centers. For example, compounds selected from (S)-naproxen-(S)-2-butyl ester, (S)-naproxen-(R)-2-butylester, (S)-naproxol-(R)-2-methyl butyrate, (S)-naproxol-(S)-2-methyl butyrate, diasteromeric mixtures of (S)-naproxen-(S)-2-butyl ester and (S)-naproxen- (R)-2-butyl ester, and diasteromeric mixtures of (S)-naproxol-(R)-2-methyl butyrate and (S)-naproxol-(S)-2-methyl butyrate are useful in the subject invention.

Finally, so-called "natural" anti-inflammatory agents are useful in methods of the subject invention. For example, candelilla wax, alpha bisabolol, aloe vera, Manjistha (extracted from plants in the genus Rubis, particularly *Rubia Cordifolia*), and Guggal (extracted from plants in the genus Commiphom, particularly *Commiphora Mukul*), may be used.

Another preferred composition useful in the subject invention comprises an anti-wrinkle agent, a sunscreen, and an anti-inflammatory agent together for wrinkle regulation in the amounts disclosed for each individually hereinabove.

C. Anti-Oxidants/Radical Scavengers

In a preferred wrinkle regulating composition useful in the subject invention, an anti-oxidant/radical scavenger is included as an active along with the anti-wrinkle agent. The inclusion of an anti-oxidant/radical scavenger increases the wrinkle regulating benefits of the composition.

A safe and effective amount of an anti-oxidant/radical scavenger may be added to the compositions useful in the subject invention, preferably from about 0.1% to about 10%, more preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, amino-guanidine), sulfhydryl compounds (e.g., glutathione), and dihydroxy fumaric acid and its salts may be used.

In a preferred wrinkle regulating composition useful in the subject invention, compositions comprise one, any two, or all three of a sunscreening agent, anti-inflammatory agent, and/or an anti-oxidant/radical scavenging agent included as actives along with the anti-wrinkle agent. The inclusion of two or all three of these agents with the anti-wrinkle agent increases the wrinkle regulating benefits of the composition.

D. Chelators

In a preferred wrinkle regulating composition useful in the subject invention, a chelating agent is included as an active along with the anti-wrinkle agent. As used herein, "chelating agent" means an active agent capable of removing a metal ion from a system by forming a complex so that the metal ion cannot readily participate in or catalyze chemical reactions. The inclusion of a chelating agent increases the wrinkle regulating benefits of the composition.

A safe and effective amount of a chelating agent may be added to the compositions useful in the subject invention, preferably from about 0.1% to about 10%, more preferably from about 1% to about 5%, of the composition. Chelators useful in compositions are disclosed in U.S. patent application Ser. No. 619,805, Bissett, Bush & Chatterjee, filed Nov. 27, 1990 (which is a continuation of U.S. patent application Ser. No. 251,910, filed Oct. 4, 1988); U.S. patent application Ser. No. 514,892, Bush & Bissett, filed Apr. 26, 1990; and U.S. patent application Ser. No. 657,847, Bush, Bissett & Chatterjee, filed Feb. 25, 1991; all incorporated herein by reference. Preferred chelators useful in compositions of the subject invention are furildioxime and derivatives thereof.

In a preferred wrinkle regulating composition useful in the subject invention, compositions comprise one, any two, any three, or all four of a sunscreening agent, anti-inflammatory agent, anti-oxidant/radical scavenging agent, and/or chelating agent included as actives along with the anti-wrinkle agent. The inclusion of two, three, or all four of these agents with the anti-wrinkle agent increases the wrinkle regulating benefits of the composition.

E. Retinoids

In a preferred wrinkle regulating composition useful in the subject invention, a retinoid, preferably retinoic acid, is included as an active along with the anti-wrinkle agent. The inclusion of a retinoid increases the wrinkle regulating benefits of the composition. A safe and effective amount of a retinoid may be added to the compositions useful in the subject invention, preferably from about 0.001% to about 2%, more preferably from about 0.01% to about 1% of the composition. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid.

In a preferred wrinkle regulating composition useful in the subject invention, compositions comprise one, any two, any three, any four, and/or all five of a sunscreening agent, anti-inflammatory agent, anti-oxidant/radical scavenging agent, chelating agent, and/or a retinoid included as actives along with the anti-wrinkle agent. The inclusion of two, three, four, or all five of these agents with the anti-wrinkle agent increases the wrinkle regulating benefits of the composition.

Methods for Using the Subject Polyol Derivatives

The subject invention relates to methods for regulating wrinkles and/or atrophy in mammalian skin. Such methods comprise topical application of a safe and effective amount of an anti-wrinkle agent. The amount of anti-wrinkle agent and frequency of application will vary widely depending upon the level of wrinkling already in existence in the subject, the rate of further wrinkle formation, and the level of regulation desired. Preferred regulation of wrinkling involves preventing or retarding the formation of wrinkles. More preferred regulation of wrinkling involves effacement of existing wrinkles.

A safe and effective amount of anti-wrinkle agent in a topical composition is applied, generally from about 0.001 $\mu$g to about 1000 $\mu$g per $cm^2$ skin per application, preferably from about 1 $\mu$g to about 500 $\mu$g/$cm^2$ skin per application, more preferably from about 10 $\mu$g to about 300 $\mu$g/$cm^2$ skin, also preferably from about 20 $\mu$g to about 200 $\mu$g/$cm^2$ skin. Application preferably ranges from about weekly to about 10 times daily, more preferably from about twice a week to about four times a day, more preferably still from about three times a week to about twice a day; also preferably about once a day. A minimum of about four weeks of treatment is preferred for an age repair benefit, more preferably a minimum of eight weeks, more preferably still a minimum of twelve weeks.

A preferred method of the subject invention for regulating wrinkles in mammalian skin involves applying both a safe and effective amount of the anti-wrinkle agent and a safe and effective amount of one or more of a sunscreening agent, an anti-inflammatory agent, an anti-oxidant/radical scavenging agent, a chelating agent and/or a retinoid to the skin simultaneously. As used herein, "simultaneous application" or "simultaneously" means applying the agents to the skin at the same sites on the body at about the same time. Though this can be accomplished by applying the agents separately to the skin, preferably a composition comprising all the desired agents commingled is applied to the skin. The amount of sunscreening agent applied is preferably from about 0.05 mg to about 0.5 mg per $cm^2$ skin. The amount of anti-inflammatory agent applied is preferably from about 0.005 mg to about 0.5 mg, more preferably from about 0.01 mg to about 0.1 mg per $cm^2$ skin. The amount of anti-oxidant/radical scavenging agent preferably applied is from about 0.01 mg to about 1.0 mg, more preferably from about 0.05 mg to about 0.5 mg per $cm^2$ skin. The amount of chelating agent preferably applied is from about 0.001 mg to about 1.0 mg, more preferably from about 0.01 mg to about 0.5 mg, still more preferably from about 0.05 mg to about 0.1 mg per $cm^2$ skin. The amount of retinoid applied is preferably from about 0.001 mg to about 0.5 mg per $cm^2$ skin, more preferably from about 0.005 mg to about 0.1 mg per $cm^2$ skin. The amount of anti-wrinkle agent applied is preferably from about 0.001 mg to about 2 mg per $cm^2$ skin per application, more preferably from about 0.01 mg to about 1 mg per $cm^2$ skin per application.

Another preferred method of the subject invention involves application of a safe and effective amount of the anti-wrinkle agent in a conductive cream or gel, followed by controlled application of an electric field having a polarity such as to drive the negatively-charged anti-wrinkle agent into the skin. This method, known as cathodal iontophoresis, is described in A. K. Banga and Y. W. Chien, "Iontophoretic Delivery of Drugs: Fundamentals, Developments, and Biomedical Applications" *J. Controlled Release* Vol. 7, pp. 1–24 (1988) and references therein, incorporated herein by reference. Further examples are given in R. R. Burnette, "Iontophoresis," J. Hadgraft and R. H. Guy (editors), *Transdermal Drug Delivery: Developmental Issues and Research Initiatives,* Marcel Dekker, New York, N.Y., 1989, pp. 247–291 and references therein and in G. B. Kasting, E. W. Merritt, and J. C. Keister, "An In Vitro Method for Studying the Iontophoretic Enhancement of Drug Transport Through Skin," *Journal of Membrane Science,* Vol. 35, pp. 137–159, (1988), and references therein, incorporated herein by reference. In such a method the solution of anti-wrinkle agent is applied to the skin and contacted by the cathode of an electrical device suitable for delivering a controlled voltage or current to the skin. The circuit is completed by placing the anode of the device on the skin at a point removed from the site of delivery. The electrical field (i.e., voltage or current) may be either pulsed, sinusoidal, or continuous wave as described in the above references. The duration of application of the field ranges from about 1 minute to about 24 hours, preferably from about 1 to about 30 minutes, more preferably from about 2 to about 5 minutes. A series of high voltage pulses followed by continuous cathodic iontophoresis as described in M. R. Prausnitz, V. G. Bose, R. Langer, and J. C. Weaver, "Electroporation of Mammalian Skin: A Mechanism to Enhance Transdermal Drug Delivery," *Proceedings of the National Academy of Sciences (USA),* Vol. 90, pp. 10504–10508, (1993) and references therein, incorporated herein by reference, may also be used. In all cases the electric field is applied in a safe and effective manner, so that the anti-wrinkle agent is delivered across the skin without undue discomfort or irritation to the subject.

The subject polyol derivatives may also be useful for one or more of the following: regulating dryness in the skin, making the complexion more even by reducing uneven pigmentation, regulating dark circles under the eyes, reducing pore size, improving the color/glow/rosiness of the skin, reducing sagging and improving the firmness of the skin, and making the skin more smooth.

The following examples further describe and demonstrate the preferred embodiments within the scope of the subject invention. The examples are given solely for the purpose of illustration, and are not to be construed as limitations of the subject invention since many variations thereof are possible without departing from its spirit and scope.

EXAMPLES 1-3

A simple solution is prepared by combining the following components using conventional mixing techniques:

| COMPONENT | EXAMPLE NO. | | |
|---|---|---|---|
| | 1 | 2 | 3 |
| myo-inositol hexakisphosphate, dodecasodium salt | 1 | — | — |
| myo-inositol hexakissulfate, hexapotassium salt | — | 2 | — |
| myo-inositol hexakis phosphoric acid (phytic acid), 50% solution in water | — | — | 10 |

-continued

| COMPONENT | EXAMPLE NO. | | |
|---|---|---|---|
| | 1 | 2 | 3 |
| 99% triethanolamine | — | — | 5 |
| phosphoric acid, 85% | 0.25 | 0.25 | — |
| propylene glycol | 30 | 30 | 30 |
| ethanol, absolute | 20 | 20 | 20 |
| deionized water | Balance to 100% | | |

This composition is useful for topical application to regulate skin wrinkles. The composition is applied to the skin at a level of 1 mg/cm$^2$ once per day for a period of six months. Cathodic iontophoresis for 2 minutes per application at a current density of 0.050 ma/cm$^2$ is used to enhance the delivery of the anti-wrinkle agent into the skin.

EXAMPLES 4–7

An oil-in-water emulsion is prepared by combining the following components using conventional mixing techniques.

| COMPONENT | EXAMPLE NO | | | |
|---|---|---|---|---|
| | 4 | 5 | 6 | 7 |
| myo-inositol hexakis sulfuric acid, 50% solution in water | 6 | — | — | — |
| myo-inositol hexakis phosphoric acid (phytic acid), 50% solution in water | — | 4 | — | — |
| 1,2,3,4,5-cyclopentanepentolsulfuric acid | — | — | 6 | — |
| 1,2,3,4,5,6,7-cycloheptaneheptolphosphoric acid | — | — | — | 6 |
| Glycerin | 3 | 3 | 3 | 3 |
| Methyl paraben | 0.2 | 0.2 | 0.2 | 0.2 |
| Steareth 20 (Brij 78R) | 1 | 1 | 1 | 1 |
| Glyceryl monostearate and PEG 100 (Arlacel 165R) | 0.5 | 0.5 | 0.5 | 0.4 |
| Carbopol 940 | 0.2 | 0.2 | 0.2 | 0.2 |
| Cetyl alcohol | 1 | 1 | 1 | 1 |
| Stearyl alcohol | 1 | 1 | 1 | 1 |
| Propyl paraben | 0.1 | 0.1 | 0.1 | 0.1 |
| Di-isopropyl dimerate | 2 | 2 | 2 | 2 |
| C$_{12}$–C$_{15}$ alcohol benzoate | 6 | 6 | 6 | 6 |
| Imidazolidinal urea | 0.3 | 0.3 | 0.3 | 0.3 |
| Ammonium hydroxide, 30% solution | 1.6 | 1.6 | 1.6 | 1.6 |
| Deionized Water | Balance to 100% | | | |

The composition is useful for topical application to regulate skin wrinkles. An amount of the composition sufficient to deposit 20 μg/cm$^2$ of the anti-wrinkle agent to the skin is used. The composition is applied twice per day for the subjects' lifetime.

EXAMPLES 8–11

A clear gel is prepared by combining the following components utilizing conventional mixing techniques.

| COMPONENT | EXAMPLE NO | | | |
|---|---|---|---|---|
| | 8 | 9 | 10 | 11 |
| myo-inositol hexakis phosphoric acid, 50% solution in water | 0.5 | — | — | — |
| myo-inositol hexakis sulfuric acid, 50% solution in water | — | 0.5 | — | — |
| myo-inositol hexakis phosphoric acid, 50% solution in water | — | — | 2 | — |
| myo-inositol hexakis sulfonic acid, 50% solution in water | — | — | — | 2 |
| Carbopol 980 | 0.55 | 0.5 | 0.5 | 0.5 |
| Disodium EDTA | 0.02 | 0.02 | 0.02 | 0.02 |
| 99% triethanolamine | 2 | 1.2 | 2 | 1.2 |
| Propylene glycol | 3 | 3 | 3 | 3 |
| Methyl paraben | 0.2 | 0.2 | 0.2 | 0.2 |
| Deionized Water | Balance to 100% | | | |

This composition is useful for topical application to regulate skin wrinkles. An amount of the composition sufficient to deposit 10 μg/cm$^2$ of anti-wrinkle agent to the skin is used. The composition is applied three times per day for one year.

EXAMPLES 12–15

An oil-in-water polymer emulsion is prepared by combining the follwing components using conventional mixing techniques.

| COMPONENT | EXAMPLE NO | | | |
|---|---|---|---|---|
| | 12 | 13 | 14 | 15 |
| myo-inositol hexakis phosphoric acid, 50% solution in water | 3 | — | — | — |
| myo-inositol hexakis sulfuric acid, 50% solution in water | — | 0.1 | — | — |
| myo-inositol hexakisphosphate, cetyltrimethylammonium salt | — | — | 0.1 | — |
| myo-inositol hexakisphosphate, cetylpyridinium salt | — | — | — | 0.1 |
| Carbopol 954 | 0.2 | 0.2 | 0.2 | 0.2 |
| Pemulen TR-2 | 0.15 | 0.15 | 0.15 | 0.15 |
| Glycerin | 3 | 3 | 3 | 3 |
| Cetyl palmitate | 2 | 2 | 2 | 2 |
| Stearoxy trimethylsilane and stearyl alcohol | 1 | 1 | 1 | 1 |
| Squalane | 6 | 6 | 6 | 6 |
| Propyl paraben | 0.1 | 0.1 | 0.1 | 0.1 |
| Methyl paraben | 0.2 | 0.2 | 0.2 | 0.2 |
| Imidazolidinol urea | 0.3 | 0.3 | 0.3 | 0.3 |
| Ammonium hydroxide, 30% solution | 5 | 3 | — | — |
| 99% triathanolamine | — | — | 0.35 | 0.35 |
| Deionized Water | Balance to 100% | | | |

This composition is useful for topical application to regulate skin wrinkles. An amount of the composition sufficient to deposit 1 μg/cm$^2$ of anti-wrinkle agent to the skin is used. The composition is applied once per week over a three-year period.

EXAMPLES 16–19

An oil-in-water microemulsion is prepared by combining the following components using conventional mixing techniques.

| COMPONENT | EXAMPLE NO | | | |
|---|---|---|---|---|
| | 16 | 17 | 18 | 19 |
| myo-inositol hexakisphosphate, dodecasodium salt | 1.5 | — | — | — |
| myo-inositol hexakissulfate, hexasodium salt | — | 1.5 | — | — |
| myo-inositol hexakis phosphoric acid, 50% solution in water | — | — | 3 | — |
| myo-inositol hexakis sulfuric acid, 50% solution in water | — | — | — | 3 |
| phosphoric acid, 85% solution | 0.4 | 0.2 | — | — |
| Ammonium hydroxide, 30% solution | — | — | 1.5 | 1 |
| PEG4 sorbitan monolaurate | 22.5 | 22.5 | 22.5 | 22.5 |
| PEG5 sorbitan monooleate | 2.5 | 2.5 | 2.5 | 2.5 |
| Cetearyl octanoate | 25 | 25 | 25 | 25 |
| DMDM hydantoin and 3-iodo-2-propynylbutyl carbamate (Glydant Plus) | 0.2 | 0.2 | 0.2 | 0.2 |
| Deionized Water | Balance to 100% | | | |

This composition is useful for topical application to regulate skin wrinkles. An amount of the composition sufficient to deposit 20 µg/cm² of anti-wrinkle agent to the skin is used. The composition is applied three time per week over a five-year period.

While particular embodiments of the subject invention have been described, it will be obvious to those skilled in the art that various changes and modifications of the subject invention can be made without departing from the spirit and scope of the invention. The appended claims are intended to cover all such modifications that are within the scope of the invention.

What is claimed is:

1. A method of regulating wrinkles in mammalian skin comprising topically applying to the skin of a mammal in need of treatment a composition comprising:
   a) a safe and effective amount of a cyclic polyanionic polyol derivative having the structure:

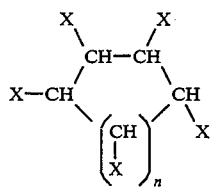

wherein n is an integer from 1 to 3; and each X is, independently, selected from the group consisting of $OSO_3^-$, $SO_3^-$, $OPO_3^=$, $PO_3^=$, $CO_2^-$, and OH; with at least 3 X's being other than OH;
   b) cations which balance the charge of the derivative of a); and
   c) a topical carrier.

2. The method of claim 1 wherein:
   a) at least 4 X's are other than OH;
   b) n is 1 or 2.

3. The method of claim 2 wherein each X is, independently, selected from the group consisting of $OPO_3^=$, $OSO_3^-$, and OH.

4. The method of claim 3 wherein:
   a) n is 2; and
   b) at least 5 X's are other than OH.

5. The method of claim 4 wherein the composition comprises a cation selected from the group consisting of $H^+$, $Na^+$, $K^+$, $Ca^{++}$, $Mg^{++}$, $Al_2(OH)_5^+$, $NH_4^+$, $(HOCH_2CH_2)_3NH^+$, $(CH_3CH_2)_3NH^+$, $HOCH_2(CH_3)_2CNH_3^+$, $(HOCH_2)_3CNH_3^+$, $CH_3(HOCH_2)_2CNH_3^+$, $CH_3CH_2(HOCH_2)_2CNH_3^+$, $(CH_3CH_2)_4N^+$, $C_{16}H_{33}(CH_3)_3N^+$, $(N-C_{16}H_{33})C_5H_4N^+$, and mixtures thereof.

6. The method of any of claims 1 or 5 wherein all non-OH X's are the same.

7. The method of claim 5 wherein the composition comprises a cation selected from the group consisting of $H^+$, $Na^+$, $K^+$, $NH_4^+$, $(HOCH_2CH_2)_3NH^+$, $HOCH_2(CH_3)_2CNH_3^+$, $(HOCH_2)_3CNH_3^+$, $CH_3(HOCH_2)_2CNH_3^+$, and mixtures thereof.

8. The method of claim 7 wherein the composition comprises a cation selected from the group consisting of $H^+$, $Na^+$, $NH_4^+$, $HOCH_2(CH_3)_2CNH_3^+$, $(HOCH_2)_3CNH_3^+$, $CH_3(HOCH_2)_2CNH_3^+$, or mixtures thereof.

9. The method of claim 8 wherein the composition comprises from about 0.5% to about 5% of the polyol derivative.

10. The method of claim 5 wherein all 6 X's are other than OH.

11. The method of claim 10 wherein X is $OSO_3^-$.

12. The method of claim 10 wherein X is $OPO_3^=$.

13. The method of any of claims 1 or 5 wherein:
   a) the composition is applied from about once a week to about 10 times a day, for a period of 4 weeks or more; and
   b) the amount of polyol derivative applied to the skin is from about 0.001 µg/cm² skin to about 1000 µg/cm² skin.

14. The method of any of claims 1 or 5 wherein the polyol is delivered into the skin by cathodal iontophoresis.

15. The method of any of claims 1 or 5 wherein the amount of polyol derivative applied to the skin is from about 1 µg/cm² skin to about 500 µg/cm² skin, from about twice a week to about 4 times a day.

16. The method of any of claims 1 or 5 wherein the composition comprises less than 1% by weight of $Cl^-$.

17. The method of any of claims 1 or 5 wherein the composition is substantially free of $CO_3^=$.

18. The method of any of claims 1 or 5 wherein the composition comprises about 0.5% or more by weight of one or more of the following: inorganic phosphate, $SO_4^=$, or a combination of inorganic phosphate and $SO_4^=$.

19. A composition for topical application for regulating wrinkles in mammalian skin comprising:
   a) a safe and effective amount of a cyclic polyanionic polyol derivative having the structure:

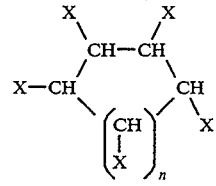

wherein n is an integer from 1 to 3; and each X is, independently, selected from the group consisting of $OSO_3^-$, $SO_3^-$, $OPO_3^=$, $PO_3^=$, $CO_2^-$, and OH; with at least 3 X's being other than OH;
   b) cations which balance the charge of the derivative of a);
   c) a safe and effective amount of a sunscreen; and
   d) a topical carrier comprising an emollient.

20. The composition of claim 19 wherein:
   a) X is $OPO_3^=$;
   b) n is 1 or 2; and
   c) at least 5 X's are other than OH.

21. The composition of claim 20 wherein:
   (a) X is $OPO_3^=$; and
   (b) n is 2.

* * * * *